United States Patent [19]

Chou et al.

[11] Patent Number: 5,570,445

[45] Date of Patent: Oct. 29, 1996

[54] REUSABLE OPTICAL FIBER CONNECTOR ADAPTER WITH PLURALITY OF OPTICAL BARRIERS FOR ALL FIBER DELIVERY LASER SOURCES

[75] Inventors: Marilyn M. Chou; King J. J. Yu; Ken T. Yu, all of Oakland, Calif.

[73] Assignee: Xintec Corporation, Oakland, Calif.

[21] Appl. No.: 496,342

[22] Filed: Jun. 29, 1995

Related U.S. Application Data

[63] Continuation-in-part of Ser. No. 264,079, Jun. 22, 1994, Pat. No. 5,452,391.

[51] Int. Cl.$^6$ .................................................. G02B 6/36
[52] U.S. Cl. ............................. 385/92; 385/78; 385/902; 606/11
[58] Field of Search ............................... 385/31, 38, 53, 385/60, 76–78, 86–88, 92, 117–119, 123, 125, 147, 902; 606/2, 10–12, 13, 16, 17

[56] References Cited

U.S. PATENT DOCUMENTS

| | | | |
|---|---|---|---|
| 4,273,109 | 6/1981 | Enderby | 385/77 X |
| 4,583,539 | 4/1986 | Karlin et al. | 385/125 X |
| 4,633,872 | 1/1987 | Chaffee et al. | 606/11 |
| 4,707,073 | 11/1987 | Kocher | 385/902 X |
| 4,722,337 | 2/1988 | Losch et al. | 606/16 |
| 4,785,805 | 11/1988 | Joffe et al. | 606/16 X |
| 4,895,145 | 1/1990 | Joffe et al. | 606/11 |
| 5,085,492 | 2/1992 | Kelsoe et al. | 385/60 |
| 5,104,242 | 4/1992 | Ishikawa | 385/53 |
| 5,116,329 | 5/1992 | Vannus et al. | 606/11 |
| 5,136,676 | 8/1992 | Arnett et al. | 385/119 |
| 5,348,487 | 9/1994 | Marazzi et al. | 385/78 X |
| 5,363,460 | 11/1994 | Marazzi et al. | 385/77 X |
| 5,452,391 | 9/1995 | Chou et al. | 385/92 |

*Primary Examiner*—John D. Lee
*Attorney, Agent, or Firm*—Ray K. Shahani, Esq.

[57] ABSTRACT

A reusable connector adapter for coupling any fiber optic transmittable laser source to a fiber optic laser delivery device, the laser source having a laser energy output port. The adapter allows the use of a variety of different laser sources with a variety of different fiber optic laser delivery devices. The adapter maintains the fiber optic laser delivery device adjacent to the laser energy output port such that the laser energy to be transmitted is communicated efficiently to the fiber optic laser delivery device. The adapter further comprises a laser interlock deactivation means such that if a laser source has a mechanical, electrical or optical interlock system, the adapter will function to deactivate the interlock system. Furthermore, the adapter also comprises a plurality of optical barriers to prevent the unintended transmission of laser energy when, for example, the fiber optic laser delivery device has not been installed or has not been installed properly.

24 Claims, 3 Drawing Sheets

REUSABLE OPTICAL FIBER CONNECTOR ADAPTER WITH PLURALITY OF OPTICAL BARRIERS FOR ALL FIBER DELIVERY LASER SOURCES

RELATED APPLICATIONS

The present application is a continuation-in-part application of application, Ser. No. 08/264,079 filed 6/22/94 (now U.S. Pat. No. 5,452,391). The complete specification, drawings and claims are incorporated herein in their entirety.

FIELD OF THE INVENTION

This invention relates generally to laser delivery systems and related accessories, and more particularly to a device which will allow the use of a variety of optical fiber laser delivery devices, systems or other optical laser transmission devices, manufactured for medical, industrial and commercial applications, with various connection means, in conjunction with any or all wavelength of laser generating sources that can be delivered through fiber optic waveguides, cables, or other optical transmission means.

BACKGROUND OF THE INVENTION

Although the first useful lasers were developed in the 1960's, recent advances in laser and fiber optic delivery systems have greatly enhanced the use of this technology in the field of medicine and other fields. Today there is a wide variety of laser delivery systems available on the market intended for use in a wide range of applications.

A common type of laser known as a CO2 laser delivers radiation with a wavelength of 10.64 microns. However, in order to focus or channel the radiated energy produced by a CO2 laser it is necessary to configure sets of mirrors in certain ways. These systems are typically large and expensive. With the advent of the Nd:YAG type laser delivering electromagnetic energy at a wavelength of 1.064 microns, it became possible to generate and focus the laser radiation through a silica core optical fiber. Recently, use of the Holmium:YAG, Erbium:YAG, pulsed dye, diode, excimer, Alexandrite, ruby, Ti:Sapphire, KTP and Argon lasers have become more widespread as new applications are being developed. Thus, fiber optic surgical tools have become important in certain procedures. The range of their utility is still being explored and discovered.

In medical applications, laser energy and optical fibers are used in different ways, including incision, necrosis or killing of live tissue, excision or removal of tissue and structure, removal of surface layers of skin, tattoos, etc., and cauterization of tissue. Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. In practice, during an incision procedure cauterization of the incised tissue is likely to occur simultaneously. Thus, laser surgery is often characterized by an absence of bleeding during the surgery, both in open and endoscopic protocols.

Given the recent advances in related surgical and other laser technology, it has become increasingly important to provide users of such equipment with a range of specific tools, accessories and laser generating systems. Many manufacturers are engaged in these activities. A range of laser drivers or laser generators are now in use in hospitals and clinics throughout the world. These laser systems are expensive and constitute major capital investments. Additionally, there is a very broad range of accessories to be used with these laser systems. Unfortunately, the laser systems available to the surgeon are not always compatible with the fiber optic accessories that the surgeon needs.

On a laser generating system there is always an output interface between the device generating the laser energy and the device transmitting the laser energy. This interface must provide several functions. First, the interface must be convenient to use. Bayonet mounted, screw-in or other quick-connect means are often provided on the laser generators. Similarly, most fiber optic scalpels, probes and other devices incorporate a factory preassembled fiber connector to be used with a specific type of laser generator. In the industry, there are several types of fiber connectors which have become standard and are used widely, due either to market share of certain manufacturers as well as industry standards which have been developed in the last decade or two. One such standard connector is known as the SMA 905 connector. Another is the proprietary design laser delivery device or other laser peripheral device connector called the EZ Connector (trademark of Xintec Corporation). The fiber optic waveguide is connected to a metal tip which aligns and directs the beam into the fiber. This metal tip is affixed to the optical fiber. A bayonet type connector has a spring loaded mounting system (or some sort of keyed, insert and turn to lock) so that the tip can be brought into close contact or adjacent position with the output port of a laser source. Thus, as the spring is elongated and the bayonet mounting is employed, the fiber connector will ensure an efficient and safe transmission of laser energy into the proximal end of the optical fiber. Other types of connectors, such as the EZ Connector and others, generally have some sort of system whereby the proximal end of the fiber is positioned precisely and the fiber connector itself maintains the integrity of the interface between the laser source and the optical fiber instrument. It is important to note that the present invention includes the embodiment wherein a bare fiber is inserted into the multi-use connector adapter.

The interface assembly must provide an accurate and precise connection and transmission of the laser energy. Typically, a laser driver will employ a series of lenses or other focusing apparatuses such that the output of the laser can be directed entirely or as nearly entirely as possible into the receiving end of the optical fiber accessory. Many of the connectors available today as standard equipment on laser drivers as well as associated accessories transmit significantly less than 100% of the energy available at the interface. This is due to poor design and inefficient coupling of the optical fiber assembly to the laser source.

Finally, all laser delivery systems require critical safety interlocks to safeguard against injury during operation. A stray laser beam can cause serious injury to operating room personnel or equipment or to the patient or doctor themselves. For example, an instantaneous flash of laser energy at 1.064 microns delivered at a rate between 20 and 100 watts, typical usage rates, can cause permanent eye damage, blindness or injury to other bodily tissue.

One such safety feature of laser generating systems comprises an interface assembly interlock system. This type of system insures that the laser cannot be operated unless properly connected to a delivery system. The interlock can be mechanical, electro-mechanical or electrical. In one system, an "electronic signature" is used. In this arrangement, at the laser output interface with the delivery apparatus, a distinctive electrical signal is produced by the coupling of the apparatus and the laser generator such that absent said distinctive electrical signature, the laser generator will not operate. This ensures that a proper connection is made between the laser and the delivery system and will prevent the transmission of laser energy unless and until the transmission is intended. Otherwise, stray laser beams can cause serious bodily and property damage.

The principle problem with all of the laser systems described above is that each manufacturer's equipment utilizes a slightly different connector and interface system. However, if a certain medical facility has invested in a laser generating system, the delivery system or other accessory options available to that facility are limited by the range of products manufactured by the same manufacturer of the laser generating system. There is a high degree of incompatibility among product designs and often certain laser equipment is unavailable to a medical practitioner due to the variations in laser connector designs. Although many of the accessories available today have become industry standards and commonplace among users, there is still a wide range of accessories which are manufactured by different manufacturers according to individual manufacturer's specific criteria and specifications.

U.S. Pat. No. 4,722,337 (Losch et al) discloses a medical laser peripheral and connector system having essentially two portions, a connector plug portion and a fiber portion. Both portions are fused together. Thus, after use of the delivery system, the entire assembly must be discarded since the optical fiber portion cannot be reused.

U.S. Pat No. 4,785,805 (Joffe et al) discloses a two piece disposable laser delivery system which is also comprised of two separable portions. One portion, the distal detachable tip, is reusable while the other portion is disposable and can be replaced. However, the reusable portion is designed to be used only with a specific type of disposable portion and is, therefore, not suitable for use with other disposable fiber optic delivery systems.

It is therefore an object of this invention to overcome the limitations of the above cited products, namely inherent design non-compatibility between various types of commercially available laser equipment, including laser generators and delivery systems.

SUMMARY OF THE INVENTION

This invention is designed to bridge the gap between industry standard laser peripherals and accessories and those manufactured to less common specifications. This invention will allow owners and users of different types of fiber optic or other laser delivery devices and laser sources to use non-standard or other peculiarly designed accessories and laser sources interchangeably.

We disclose a reusable connector adapter for coupling any fiber optic transmittable laser source to a fiber optic laser delivery device, the laser source having an output port for transmitting laser energy, the fiber optic laser delivery device having a laser receiving end with a fiber connector at the laser receiving end, and the fiber optic laser delivery device further having a fiber optic waveguide. The reusable connector adapter comprises a connector plug portion, the connector plug portion having a proximal end precisely shaped so as to couple efficiently with the laser source, the proximal end of the connector plug portion having a laser source attachment means such that the connector plug portion can be securely maintained adjacent to the output port of the laser source in an operative position, the connector plug portion further having a distal end, and the connector plug portion further having a central hollow body portion intermediate the proximal end and the distal end for receiving and containing the fiber connector within the central hollow body portion in efficient optical communication with the laser source.

The invention also comprises a fiber optic laser delivery device securing portion for removably maintaining and securing the fiber optic laser delivery device within the central hollow body portion of the connector plug portion. A first optical barrier for prevents the laser energy from being transmitted along with a second optical barrier for preventing the laser energy from being transmitted.

If the laser source has a laser interlock for preventing the undesired transmission of laser energy unless and until such time as the interlock is deactivated, the connector plug portion of the reusable connector adapter further comprises a laser interlock deactivation means. If the laser interlock comprises a mechanical switch, the laser interlock reactivation means of the reusable connector adapter can engage the mechanical switch such that the laser source interlock is deactivated. If the laser interlock requires an electrical signature generated by an electrical signature generating circuit for reactivation of the laser interlock, the laser interlock deactivation means of the reusable connector adapter further comprises an electrical signature generating circuit. Finally, if the laser interlock requires an optical signal or block for deactivation of the laser interlock, the laser interlock deactivation means of the reusable connector adapter further comprises an optical block or signal generating means.

The plurality of optical barriers prevent the laser energy from being transmitted unless a fiber optic laser delivery device is properly installed within the reusable connector adapter. The plurality of optical barriers are comprised of an optically opaque material. The plurality of optical barriers are mounted within the central hollow body portion of the connector plug portion such that upon insertion of the fiber optic laser delivery device into the reusable connector adapter, the optical barriers are removed from the path of transmission of laser energy. The second optical barrier can be disposed between the first optical barrier and the distal end of the connector plug portion, or the first optical barrier can be adjacent the proximal end of the connector plug portion. The second optical barrier can be adjacent the fiber optic laser delivery device securing portion of the reusable connector adapter. The plurality of optical barriers can be pivotally mounted on spring members, or mounted in some other fashion within the connector plug portion.

The laser interlock system might require a mechanical, electrical or optical contact between the proximal end of the connector plug portion and the output port of the laser source for deactivation, and the laser interlock deactivation means comprises a contacting element. The contacting element could be retractable, and if so, the retractable contacting element could be in a retracted position in the absence of the fiber optic laser delivery device but in an extended position when the fiber connector of the fiber optic laser delivery device is received within the connector plug portion, whereby when the retractable element is extended, the contacting element is in electrical, mechanical or optical contact with the output port of the laser source.

The fiber optic laser delivery device securing portion can comprise an engagement means for coupling the fiber optic laser delivery device securing portion to the connector plug portion, thereby maintaining the fiber optic laser delivery device within the central hollow body portion. Furthermore, the engagement means can comprise a biasing element for maintaining the fiber optic laser delivery device within the central hollow body portion biased between the connector plug portion and the fiber optic laser delivery device securing portion.

The laser interlock can comprise an optical switch, and when the laser interlock deactivation means of the reusable connector adapter supplies an optical signal, the laser source interlock can be deactivated.

The fiber connector on the fiber optic laser delivery device can be an SMA type connector. It can also be an EZ Connector.

The invention further comprises a plurality of additional optical barriers for preventing the laser energy from being transmitted.

If the laser source has a recessed output port for transmitting laser energy, extending from the proximal end of the connector plug portion there is a predetermined length of optical fiber, the predetermined length of optical fiber having a proximal end for aligning the fiber with and maintaining the fiber adjacent to the output port. The device can also comprise a sheath covering the predetermined length of optical fiber. The extending fiber portion can also have a tip portion to align the predetermined length of optical fiber with and maintain the proximal end of the predetermined length of optical fiber adjacent to the output port of the laser source.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

Figure 1A:
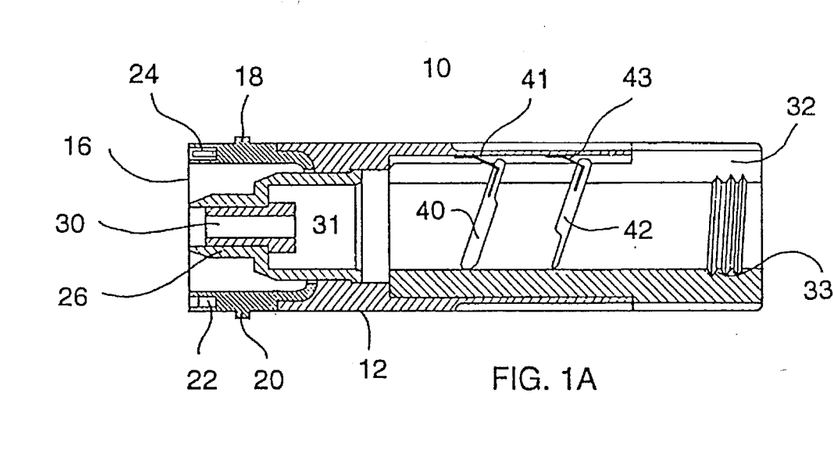
FIG. 1A is a side cross section view of the connector plug portion of an embodiment of the apparatus of the present invention.
Figure 1B:
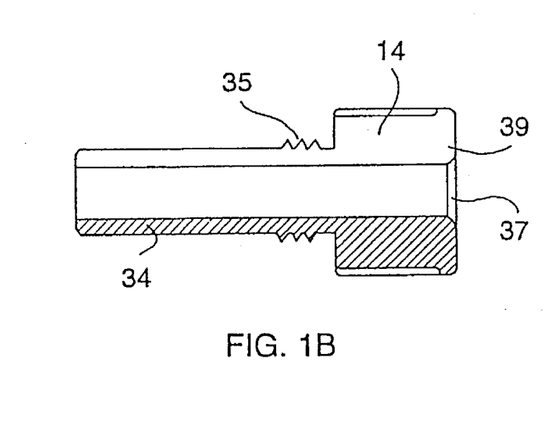
FIG. 1B is a side cross section view of the fiber securing portion of an embodiment of the apparatus of the present invention.
Figure 1C:
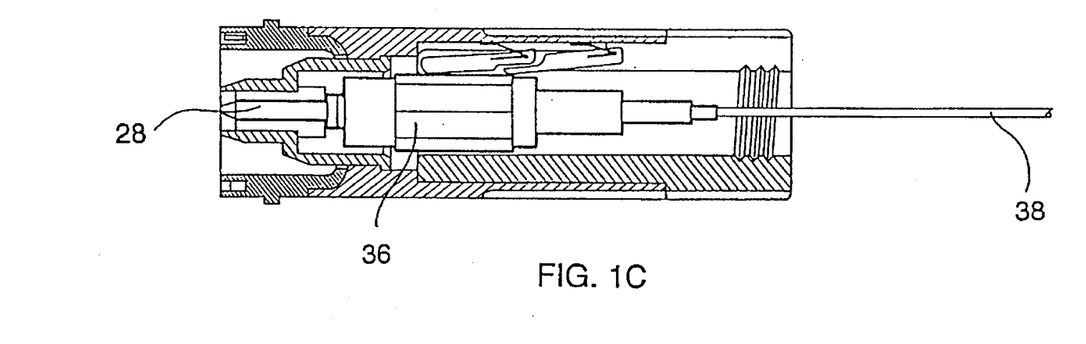
FIG. 1C is a side cross section view of an embodiment of the apparatus of the present invention showing the connector plug portion and fiber securing portion assembled with a fiber optic laser delivery device with an EZ Connector (trademark of Xintec Corporation).

FIG. 1A is a side cross section view of the connector plug portion of an embodiment of the apparatus of the present invention. FIG. 1B is a side cross section view of the fiber securing portion of an embodiment of the apparatus of the present invention. FIG. 1C is a side cross section view of an embodiment of the apparatus of the present invention showing the connector plug portion and fiber securing portion assembled with an fiber optic laser delivery device with an EZ Connector installed therein.

The multi-use connector adapter 10 is essentially comprised of two portions, the connector plug portion 12 and the fiber securing portion 14. The proximal end 16 of the connector plug portion is formed such that it is received by the output port of a laser source (not shown). Opposing tabs 18 and 20 form a bayonet-type mounting attachment means for connecting this embodiment of the connector plug portion of the multi-use connector adapter to the output port of the laser source. Any of a variety of laser source attachment means may be selected, depending upon the precise application and configuration of other equipment in use, including threads, clamps, compression fitting, or other laser source attachment means known to those skilled in the art.

A circumferential groove 22 in the proximal end of the connector plug portion of the multi-use connector adapter contains a plurality of metal contacts 24 secured therein. The presence of the metal contacts is only required if the laser source is equipped with a laser interlock system whereby the control electronics or some mechanical device or control program of the laser source prevents the transmission of laser energy unless an electronic circuit is closed. These metal contacts, therefore, serve to provide a signature signal to the control electronics of the laser source, its precise format or type of signal depending upon the requirements of the laser source interlock. Unless and until the metal contacts close the required circuit or supply the required electronic signature, the laser interlock system prevents the transmission of laser energy. This control circuit may also serve to identify to the laser source the type of laser peripheral being employed.

When the laser interlock comprises a mechanical switch, the laser interlock deactivation means can engage the mechanical switch such that the laser source interlock is deactivated. Similarly, when the laser interlock requires an electrical signature generated by an electrical signature generating circuit for deactivation of the laser interlock, or when the laser interlock requires a certain optical signal, the laser interlock deactivation means of the multi-use connector adapter further comprises a portion or all of an electrical signature generating circuit or an optical signal generating signal.

An interlock may have an optical deactivation means, and an optical signal or block may be generated by an optical signal or block generating means. This could be nothing more than a lamp and detector which, when a block is interposed between the lamp and detector, deactivates the interlock. Alternatively, a shutter or other structure could be used to block a lamp, which, when removed, would allow the lamp to generate an optical signal.

A generally conical shaped central opening 26 is formed in the proximal end of the connector plug portion so as to receive the proximal end 28 of a fiber optic laser delivery device connector 36 from the central opening 30 of the inside annular region 31 of the proximal end of the connector plug portion. This conical shaped central member forms a physical matching connection between the laser source and the fiber optic laser delivery device by positioning the proximal end of the fiber optic laser delivery device accurately and precisely adjacent to the output port of the laser source, thereby allowing laser energy to be communicated directly and efficiently from the laser source into the proximal end of the fiber optic laser delivery device. This highly efficient optical communication between the laser source and the fiber optic laser delivery device is very important to protect the integrity of the connector adapter and the laser source output port. The distal end 32 of the connector plug portion can be engaged by the proximal end 34 of the fiber securing portion of the present invention. This engagement can be accomplished by providing matching, threaded portions 33 and 35, or other adjustable and detachable or loosening connecting means such as a bayonet-type mounting or some spring-loaded connecting means. Therefore, the fiber optic laser delivery device is held securely in place by being inserted into the connector plug portion of the multi-use connector and having the fiber securing portion installed. The fiber optic laser delivery device connector 36 is held in place by being inserted into the conical shaped central member in the proximal end of the multiuse connector adapter, and by contact by the proximal end of the fiber securing portion. Although FIG. 1C shows the invention being used in conjunction with a fiber optic laser delivery device having an EZ Connector attached thereto, it is important to note that this fiber connector can be an SMA, EZ Connector or other standard or non-standard fiber connector. A slot 37 is provided in the fiber securing portion so as to allow the fiber securing portion to be slipped over the fiber optic portion of the laser delivery device and assembled efficienfiy and convenienfiy. Thus, the fiber optic portion 38 of the fiber optic laser delivery device is shown to extend from the distal end of the fiber securing portion 39 of the multi-use connector adapter.

As a safety feature of the invention, a first optical barrier 40 is placed in the connector plug portion. It could also be placed inside the conical shaped central opening or at some other point between the proximal and distal ends of the connector plug portion. This optical barrier is held in a normally closed position by a first spring 41. A second optical barrier 42 is placed inside the connector plug portion, also held in a normally closed position by a second spring 43. Thus, in the event the multi-use connector adapter is connected to a laser source and the laser source interlock system is deactivated resulting in laser energy transmission without first inserting a fiber optic laser delivery device, there will be no opportunity for the laser source to be released into the surrounding operating room or other environment. This is very important in operation. As is well known, a stray laser beam in a medical operating room or in most any other application would have the potential to cause serious damage to surgeons, technicians, patients, observers, or any equipment in the vicinity.

It will be understood that while the optical barriers are described as being operable with a spring element, the spring element can have a common type of spring structure or can have some other structure. This will include the use of a resilient tongue, the connection between the optical barrier can be of a resilient material, etc.

The apparent redundancy in this dual optical barrier design is very important—the result is a failsafe piece of equipment. In the event laser transmission is initiated before a fiber optic laser delivery device is installed, the optical barriers act as safety shutters. As discussed above, most lasers used in medical situations are operated by the surgeon or technician. Often, the laser interlock is deactivated when certain equipment is installed properly, such as a fiber optic laser delivery device manufactured with the laser-specific deactivation means built into the delivery device connection means. Then, laser energy can be transmitted when a footpedal or remote switch is operated. This multi-tiered laser activation system ensures that laser transmission only occurs when intended. The laser interlock prevents activation of the power source which drives the laser. However, once the connector adapter of the present invention is installed in the laser, the interlock is deactivated without a fiber optic laser delivery device necessarily being in place. The footpedal or activation switch could be operated manually, either intentionally or accidentally, to transmit energy.

Utilizing another type of connector adapter in a similar manner would result in deactivation of the laser interlock but a problem could arise if the footpedal or switch were accidentally depressed. Since some laser systems only allow deactivation of the interlock when a fiber optic laser delivery device is installed, this is a safety feature which is unavoidably lost when a connector adapter similar to the present invention is used. Since one of the main purposes of the present invention is to enable users of certain laser systems to use standard commercially available laser peripherals and supplies not necessarily equipped with the specifically designed laser interlock deactivation mean required by the specific systems, some means of ensuring accidental discharge of laser energy is very important. The dual optical barrier system is a solution to this problem.

If the connector adapter of the present invention is installed, the electrical, mechanical or optical laser interlock, specific to the laser being used, is deactivated. The dual optical barriers will prevent transmission of any laser energy which might be produced by the laser, say upon operation of the footpedal or switch. If the footpedal or switch were accidentally activated (for example by a piece of equipment falling on the switch or by human error), laser energy could be transmitted out the distal end of the fiber securing portion of the connector adapter with potentially extremely unfortunate consequences. In the event the laser source were activated after having the connector adapter installed, a great deal of thermal energy would impinge upon the optically proximal barrier (indicated herein as the first optical barrier 40). Any failure in this first optical barrier could have disastrous consequences. Thus, the provision of the second optical barrier 42 is another safety factor built into the present invention. Any number of optical barriers could be employed in the present invention, although two is the minimum number necessary to provide all of the safeguards and functions of the system.

FIG. 1C shows the fiber securing means securing a fiber optic laser delivery device inside the connector plug portion of the connector adapter of the present invention. The two optical barriers have been rotated up and out of the optical path through the device. The delivery device is shown as having an EZ Connector (trademark of Xintec Corporation), although the specific type of connector attachment on the fiber optic laser delivery device can be changed. The EZ Connector has a spring-biased tip 28 which, when assembled with the present invention, becomes disposed within the central opening to the central annular region of the connector adapter. As the fiber securing portion is placed over the laser delivery device and the threaded portions of the connector adapter are engaged, the proximal end of the fiber securing portion bears upon the spring-loaded connector of the laser delivery device and maintains the proximal end of the fiber optic laser delivery device connector precisely aligned with the output port of the laser source (not shown). In this manner of assembly, the fiber receives all of the laser energy transmitted from the laser source and efficiently transmits it to the point of application of the laser energy.

The material of construction of the optical barrier is very important. For one embodiment, any material which does not absorb electromagnetic energy in the infrared frequencies would be adequate so that the optical barrier doesn't get too hot or become destroyed due to incident laser energy. However, depending upon the application, the barrier can absorb or reflect, or a combination of both, and the precise design, manner of construct or materials of construction can be modified as desired. Absorption of energy could be a valuable function if overheating becomes a problem. Materials such as aluminum, stainless steel, plastics, ceramics or other metals, durametallics, composites or polymeric materials might be used, optionally with a coating or barrier to prevent absorption by the infrared laser energy, and the precise composition of the material of construction of the optical barrier would be determined depending upon the application.

Furthermore, the precise location of the optical barriers can be determined based upon the individual application or instrument design. For example, in certain embodiments it may be advantageous to have the first or proximal optical barrier placed immediately adjacent to the laser source, i.e. close to the receiving or proximal end of the connector adapter of the present invention. This would provide an initial degree of safety by preventing any transmission beyond the conical shaped central member into the central annular region of the connector adapter as much as possible. Additionally, it may be advantageous to dispose the second or distal optical barrier towards the distal end of the connector plug portion of the connector. In this manner, if laser energy is ever directed onto the second optical barrier and any damage results, any damage to the laser source itself would be minimized by displacing the second optical barrier as far back on the connector as possible. It will be understood by those skilled in the art that a plurality of designs, wherein the precise placement of the two optical barriers are disposed at various locations within the connector adapter, will be obvious. Based upon the type of laser, the type procedure, and the type of connector attached to the optical fiber laser delivery device, the optimum locations of the two optical barriers can be chosen.

It will also be understood that more than two optical barriers can be employed with the present invention. The dual-optical barrier scheme shown in the drawings of the preferred embodiments is the bare minimum required to achieve the degree of safety provided by the present design. However, as different procedures or different types of lasers are developed in the future, different design considerations may become obvious. The scope of this patent is intended to cover all of these designs and embodiments, and any number of optical barriers more than one will be incorporated herein.

Figure 2A:
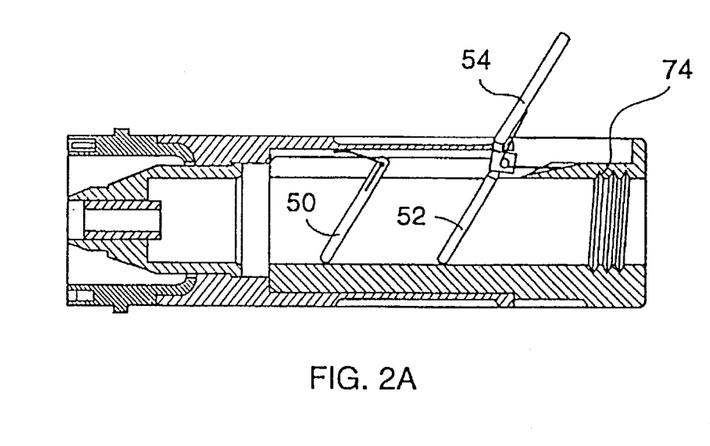
FIG. 2A is a side cross section view of the connector plug portion of an embodiment of the apparatus of the present invention.
Figure 2B:
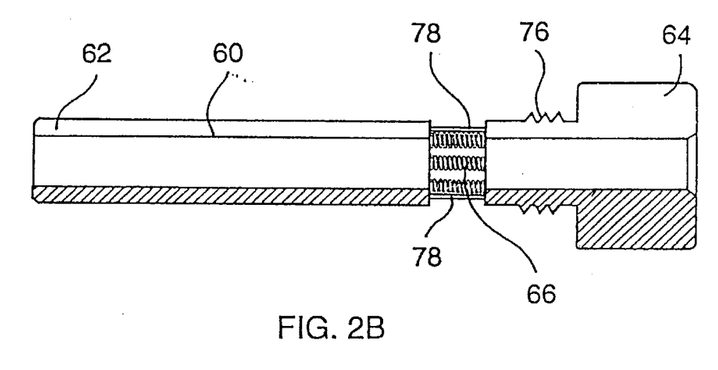
FIG. 2B is a side cross section view of the fiber securing portion of an embodiment of the apparatus of the present invention.
Figure 2C:
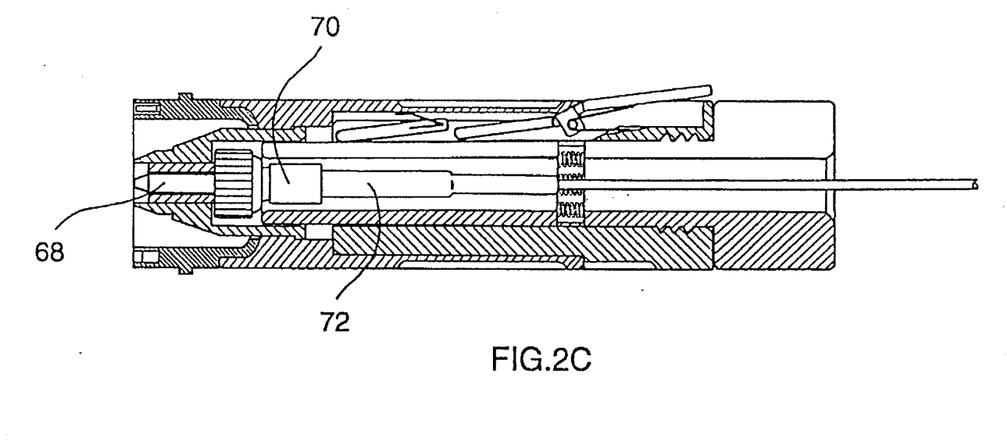
FIG. 2C is a side cross section view of an embodiment of the apparatus of the present invention showing the connector plug portion and fiber securing portion assembled with a fiber optic laser delivery device with an SMA connector.

FIG. 2A is a side cross section view of the connector plug portion of an embodiment of the apparatus of the present invention. FIG. 2B is a side cross section view of the fiber securing portion of an embodiment of the apparatus of the present invention. FIG. 2C is a side cross section view of an embodiment of the apparatus of the present invention showing the connector plug portion and fiber securing portion assembled with a fiber optic laser delivery device with an SMA connector. The embodiments shown in FIGS. 2A–2C are designed especially for use with the SMA type or similar laser connector fitting.

The first (proximal) optical barrier 52 is forward of the second (distal) optical barrier 52. However, a lever portion 54 is provided on the second optical barrier. Obviously, in the embodiment shown, as the fiber optic laser delivery device is inserted the handle need not be manually operated to allow the connector of the laser delivery device to enter the central annular region of the connector plug portion. However, to withdraw the fiber optic laser delivery device, the lever must be depressed. This manual operation is but another safety feature of the present invention.

The fiber securing portion 60 of the embodiment shown in FIG. 2B also has a proximal and a distal end (62 and 64). However, at a point located anywhere between the two ends, a plurality of biasing springs 66 are placed so as to maintain the proximal end 68 of the connector 70 of the fiber optic laser delivery device 74. In the present embodiment, since the SMA connector is not a spring-biased connector, placing one or more springs into the fiber securing portion allows the connector adapter to keep the proximal end of the fiber optic laser delivery device connector securely and firmly positioned within the connector adapter of the present invention. As the threaded portions of the connector plug portion and the fiber securing portion, 74 and 76 respectively, are engaged, the biasing springs of the fiber securing portion are compressed. This novel and useful feature of the present invention is necessary for the proper functioning of the connector adapter. Although it may be possible to construct a similar connector adapter without the biasing springs of the fiber securing portion, for example by allowing the threaded portions of the two portions to be longer and thus act in a similar manner upon the fiber optic laser delivery device connector, the biasing springs are very useful.

Furthermore, it may also be advantageous to place one or more alignment bars 78 adjacent to and parallel with the biasing springs of the fiber securing portion. These alignment bars will prevent the distal end of the fiber securing portion from turning independently from the proximal end of the fiber securing portion. These alignment bars may be very important, especially when the biasing springs are being compressed upon installation of the fiber optic laser delivery device. In the absence of such alignment bars, the biasing springs may become twisted or displaced into a position other than along an axis parallel with the central axis of the connector adapter. It would be very easy to apply an excess of torque, manually, so as to deform or destroy the biasing springs of the fiber securing portion. However, the alignment bars will prevent this deformation or twisting of the distal end of the fiber securing portion relative to the proximal end.

Figure 3A:
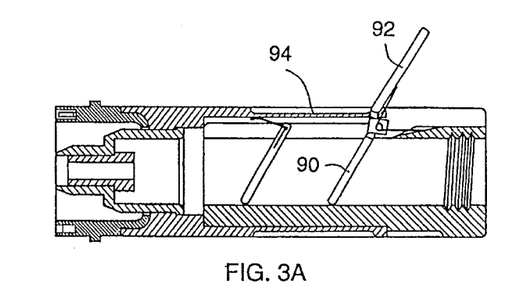
FIG. 3A is a side cross section view of the connector plug portion of an embodiment of the apparatus of the present invention.
Figure 3B:
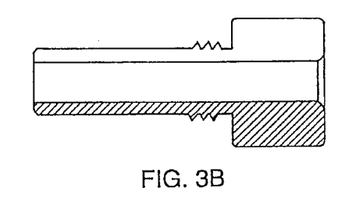
FIG. 3B is a side cross section view of the fiber securing portion of an embodiment of the apparatus of the present invention.
Figure 3C:
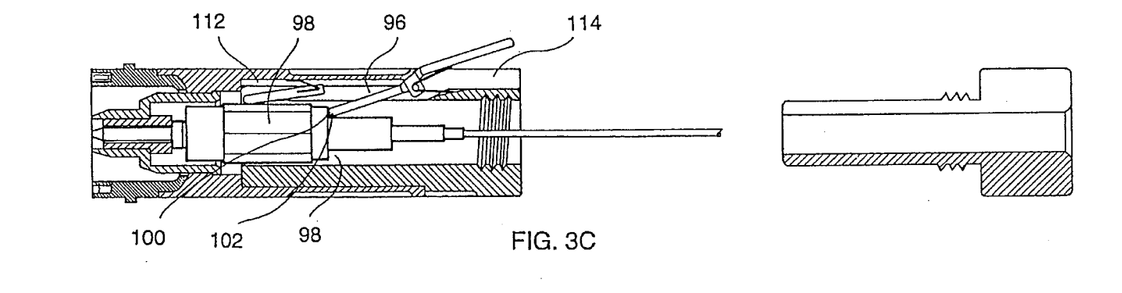
FIG. 3C is a side cross section view of an embodiment of the apparatus of the present invention showing the connector plug portion with an optical fiber laser delivery device having an EZ Connector inserted therein and a fiber securing portion in alignment therewith.
Figure 3D:
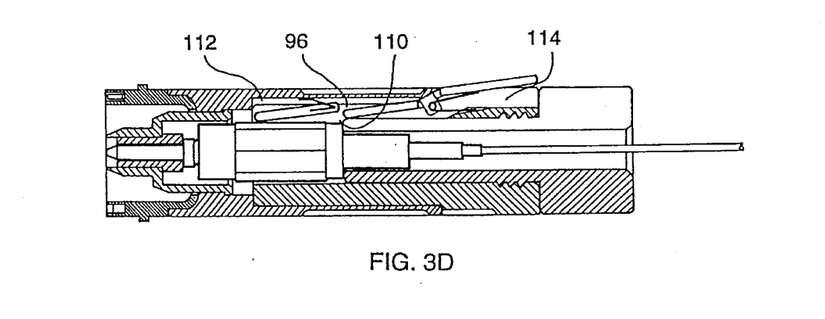
FIG. 3D is a side cross section view of an embodiment of the apparatus of the present invention showing the connector plug portion and fiber securing portion assembled with a fiber optic laser delivery device with an EZ Connector installed therein.

FIG. 3A is a side cross section view of the connector plug portion of an embodiment of the apparatus of the present invention. FIG. 3B is a side cross section view of the fiber securing portion of an embodiment of the apparatus of the present invention. FIG. 3C is a side cross section view of an embodiment of the apparatus of the present invention showing the connector plug portion with an optical fiber laser delivery device having an EZ Connector inserted therein and a fiber securing portion in alignment therewith. FIG. 3D is a side cross section view of an embodiment of the apparatus of the present invention showing the connector plug portion and fiber securing portion assembled with a fiber optic laser delivery device with an EZ Connector installed therein. It will be noted that the second (distal) optical barrier 90 has a lever 92 extending through the top portion 94 of the connector plug portion, and a distal barrier aperture 96 is provided inside the central annular region 98 of the connector plug portion.

In this embodiment, as will be apparent upon inspection of FIG. 3C, when the fiber optic laser delivery device is inserted into the connector plug portion, the second optical barrier is initially displaced. It then will bear upon the distal lip portion 100 of the main body portion of the EZ Connector at a point 102. The second optical barrier will, therefore, be maintained within the central annular region of the connector plug portion.

When the assembly is complete as shown in FIG. 3D, the proximal end 110 of the fiber securing portion will urge the optical barrier upwards into the barrier aperture. It will be obvious that a proximal barrier aperture 112 is also defined by the inside geometry of the connector plug portion. Thereafter, disassembly of the system will require the lever of the second optical barrier to be depressed into lever aperture 114 to remove the end of the optical barrier from the exit path of the fiber connector.

It is important to note that the present invention includes the embodiment wherein a bare fiber is inserted into the multi-use connector adapter. In this application, where a fiber has a bare end or other simple fitting, but is to be used to direct a laser beam, the bare fiber or other simple fitting could be inserted into the adapter. This embodiment would be slightly different than those previously described. With regard to the design of the connector plug portion, the internal annular opening for receiving the fiber connector would be somewhat smaller. Furthermore, the fiber securing portion will be designed specifically for maintaining bare fibers in close proximity with the adapter so that the entire assembly can be mounted onto a laser source output port.

Another type of laser source has a transmission port recessed inside the laser housing. Therefore, another embodiment of the reusable connector adapter of the present invention comprises a fiber extending from the proximal end of the connector plug portion. This fiber could be bare, but would optimally be covered in some sheath of a polyamide, aluminum, stainless steel or other suitable material. The fiber and any sheath would extend a predetermined distance past the proximal end of the connector plug portion so as to couple or engage the recessed output port of the laser source efficiently.

It will be understood that the embodiments shown and described herein are typical and representative of but a few of the embodiments of the present invention designed specifically for compatibility and adaptability among and between the plethora of available equipment. Therefore, modifications and slight improvements or adaptations for other configurations of laser source as well as fiber optic laser delivery device may be obvious to those knowledgeable, trained or skilled in the art. A variety of methods are available for securing connectors to fibers, interfacing the fiber optic laser delivery device with the laser output port, securing the fiber/connector assembly to the adaptor, etc. and all of these existing or future methods and designs will be incorporated herein.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A reusable connector adapter for coupling any fiber optic transmittable laser source to a fiber optic laser delivery device, the laser source having an output port for transmitting laser energy, the fiber optic laser delivery device having a laser receiving end with a fiber connector at the laser receiving end, the fiber optic laser delivery device further having a fiber optic waveguide, the reusable connector adapter comprising:

a connector plug portion, the connector plug portion having a proximal end precisely shaped so as to couple efficiently with the laser source, the proximal end of the connector plug portion having a laser source attachment means such that the connector plug portion can be securely maintained adjacent to the output port of the laser source in an operative position, the connector plug portion further having a distal end, the connector plug portion further having a central hollow body portion intermediate the proximal end and the distal end for receiving and containing the fiber connector within the central hollow body portion in efficient optical communication with the laser source;

a fiber optic laser delivery device securing portion for removably maintaining and securing the fiber optic laser delivery device within the central hollow body portion of the connector plug portion;

a first optical barrier for preventing the laser energy from being transmitted; and a second optical barrier for preventing the laser energy from being transmitted.

2. The invention of claim 1 wherein the laser source has a laser interlock for preventing the undesired transmission of laser energy unless and until such time as the interlock is deactivated and the connector plug portion of the reusable connector adapter further comprises a laser interlock deactivation means.

3. The invention of claim 2 wherein the laser interlock comprises a mechanical switch and wherein the laser interlock deactivation means of the reusable connector adapter can engage the mechanical switch such that the laser source interlock is deactivated.

4. The invention of claim 2 wherein the laser interlock requires an electrical signature generated by an electrical signature generating circuit for deactivation of the laser interlock and the laser interlock deactivation means of the reusable connector adapter further comprises an electrical signature generating circuit.

5. The invention of claim 2 wherein the laser interlock requires an optical signal or block for deactivation of the laser interlock and the laser interlock deactivation means of the reusable connector adapter further comprises an optical block or signal generating means.

6. The invention of claim 2 wherein the laser interlock system requires a mechanical, electrical or optical contact between the proximal end of the connector plug portion and the output port of the laser source for deactivation, and the laser interlock deactivation means comprises a contacting element.

7. The invention of claim 6 wherein the contacting element is retractable.

8. The invention of claim 7 wherein the retractable contacting element is in a retracted position in the absence of the fiber optic laser delivery device and in an extended position when the fiber connector of the fiber optic laser delivery device is received within the connector plug portion, whereby when the retractable element is extended, the contacting element is in electrical, mechanical or optical contact with the output port of the laser source.

9. The invention of claim 2 wherein the laser interlock comprises an optical switch and wherein the laser interlock deactivation means of the reusable connector adapter supplies an optical signal such that the laser source interlock is deactivated.

10. The invention of claim 1 wherein the first and second optical barriers prevent the laser energy from being transmitted unless a fiber optic laser delivery device is properly installed within the reusable connector adapter.

11. The invention of claim 10 wherein the first and second optical barriers are comprised of an optically opaque material.

12. The invention of claim 10 wherein the first and second optical barriers are mounted within the central hollow body portion of the connector plug portion such that upon insertion of the fiber optic laser delivery device into the reusable connector adapter, the optical barriers are removed from the path of transmission of laser energy.

13. The invention of claim 10 wherein the second optical barrier is disposed between the first optical barrier and the distal end of the connector plug portion.

14. The invention of claim 10 wherein the first optical barrier is adjacent the proximal end of the connector plug portion.

15. The invention of claim 10 wherein the second optical barrier is adjacent the fiber optic laser delivery device securing portion of the reusable connector adapter.

16. The invention of claim 10 wherein the first and second optical barriers are pivotally mounted on spring members.

17. The invention of claim 1 wherein the fiber optic laser delivery device securing portion comprises an engagement means for coupling the fiber optic laser delivery device securing portion to the connector plug portion, thereby maintaining the fiber optic laser delivery device within the central hollow body portion.

18. The invention of claim 17 wherein the engagement means comprises a biasing element for maintaining the fiber optic laser delivery device within the central hollow body portion biased between the connector plug portion and the fiber optic laser delivery device securing portion.

19. The invention of claim 1 wherein the fiber connector on the fiber optic laser delivery device is an SMA type connector.

20. The invention of claim 1 wherein the fiber connector on the fiber optic laser delivery device is an EZ Connector.

21. The invention of claim 1 further comprises a plurality of additional optical barriers for preventing the laser energy from being transmitted.

22. The invention of claim 1 wherein the laser source has a recessed output port for transmitting laser energy and extending from the proximal end of the connector plug portion there is a predetermined length of optical fiber, the predetermined length of optical fiber having a proximal end for aligning the fiber with and maintaining the fiber adjacent to the output port.

23. The invention of claim 22 further comprising a sheath covering the predetermined length of optical fiber.

24. The invention of claim 22 further comprising a tip portion on the proximal end of the predetermined length of optical fiber to align the predetermined length of optical fiber with and maintain the proximal end of the predetermined length of optical fiber adjacent to the output port of the laser source.

* * * * *